United States Patent

Straub et al.

[11] Patent Number: 5,873,882
[45] Date of Patent: Feb. 23, 1999

[54] CATHETER FOR DETACHING ABNORMAL DEPOSITS FROM BLOOD VESSELS IN HUMANS

[75] Inventors: Immanuel Straub, Wangs; Helmuth Mohr, Buchs, both of Switzerland

[73] Assignee: Straub Medical AG, Wangs, Switzerland

[21] Appl. No.: 913,952
[22] PCT Filed: Mar. 7, 1996
[86] PCT No.: PCT/CH96/00085
§ 371 Date: Sep. 29, 1997
§ 102(e) Date: Sep. 29, 1997
[87] PCT Pub. No.: WO96/29941
PCT Pub. Date: Oct. 3, 1996

[30] Foreign Application Priority Data

Mar. 28, 1995 [CH] Switzerland .............. 873/95

[51] Int. Cl.⁶ .......... A61B 17/22; A61B 17/32; A61B 17/14
[52] U.S. Cl. .......... 606/159; 606/180; 606/170
[58] Field of Search .......... 606/1, 79, 80, 606/167–174, 180, 159

[56] References Cited

U.S. PATENT DOCUMENTS

| | | |
|---|---|---|
| 4,857,046 | 8/1989 | Stevens . |
| 5,112,299 | 5/1992 | Pascaloff . |
| 5,269,751 | 12/1993 | Kaliman . |
| 5,383,884 | 1/1995 | Summers . |

FOREIGN PATENT DOCUMENTS

| | | |
|---|---|---|
| A 0582 533 | 2/1994 | European Pat. Off. . |
| A WO 91 01114 | 2/1991 | WIPO . |
| A WO 92 07500 | 5/1992 | WIPO . |

OTHER PUBLICATIONS

The Practice of Interventional Cardiology Chapter 13, Percutaneous Transluminal Coronary Rotary Ablation with the Rotablator, pp. 141–147, Michel E. Bertrand, et al.

The Practice of Interventional Cardiology Chapter 14, Coronary Atherectomy with the TEC Device, Michael H. Sketch, Jr., et al., pp. 149–155.

The Practice of Interventional Cardiology Chapter 15, Directional Coronary Atherctomy, Matthew R. Selmon, et al., pp. 157–169.

The Practice of Interventional Cardiology Chapter 16, Percutaneous Rotational Thrombectomy: An Alternative Approach to Thrombolysis, pp. 171–176, Timothy A. Dewhurst, et al.

Primary Examiner—Glenn K. Dawson
Attorney, Agent, or Firm—Oblon, Spivak, McClelland, Maier & Neustadt, P.C.

[57] ABSTRACT

The catheter connected to a drive unit has, at its front end a cutting tool which consists of a stator and rotor. Cutting edges arranged on the circumference of the rotor and stator interact in a shearing action. The rotor is an external rotor. The detached deposits are conveyed through a tubular sheath and into a collecting container via a discharge chamber. A rotary catheter of this kind is used for carefully removing blood clots and stenoses from narrowed blood vessels such as arteries and veins.

20 Claims, 4 Drawing Sheets

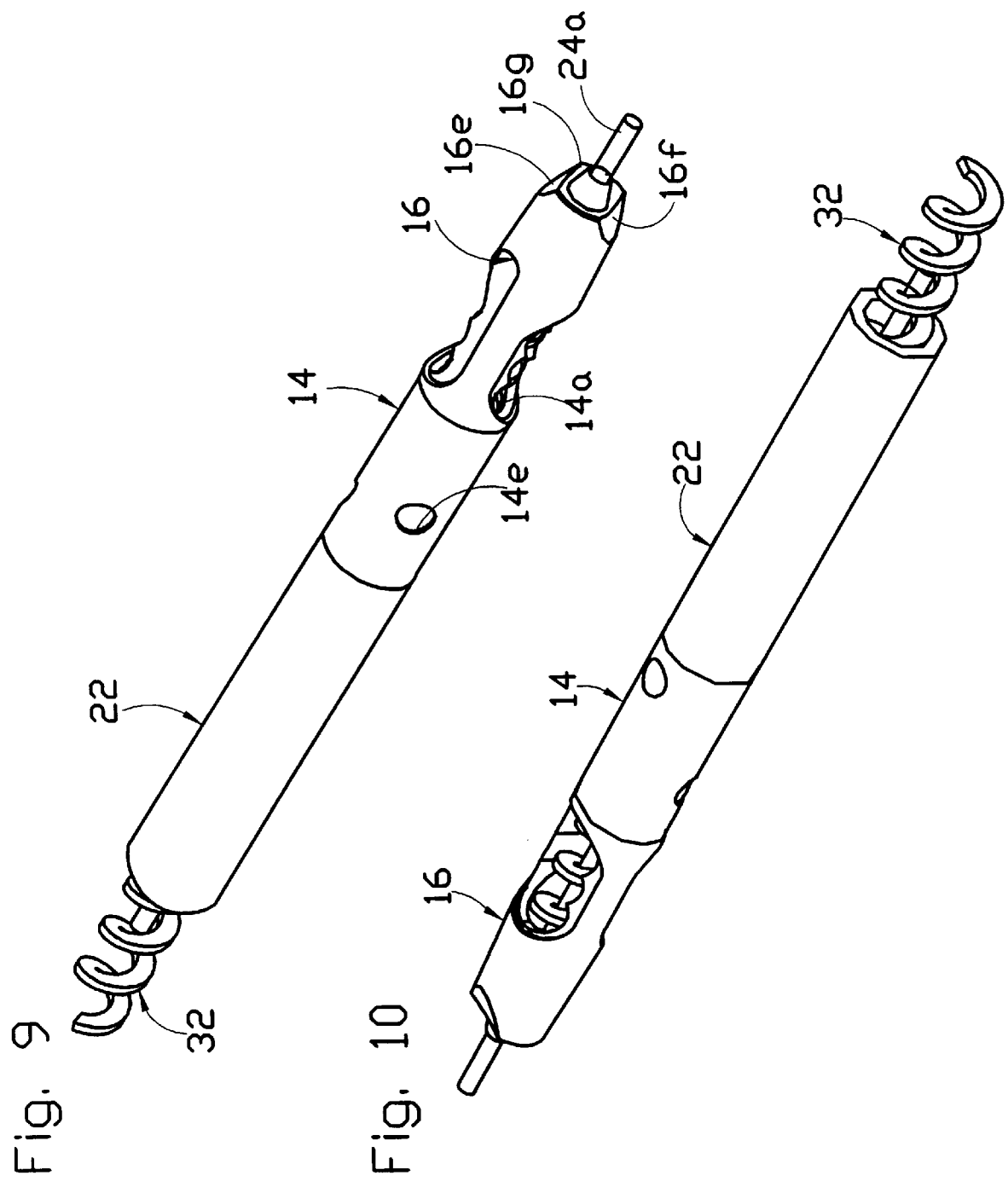

CATHETER FOR DETACHING ABNORMAL DEPOSITS FROM BLOOD VESSELS IN HUMANS

BACKGROUND OF THE INVENTION

The invention relates to a catheter of the type known as a rotary catheter.

A catheter of this kind is used in particular for treating occlusive diseases of the arteries by dislodging and breaking up stenoses and blood clots. It is introduced into the artery or vein and is advanced as far as the stenosed area which is to be treated. A cutting tool which can be driven in rotation is arranged at its front or leading end.

DISCUSSION OF THE BACKGROUND

The present invention utilizes a cutting edge which extends at least approximately in the axial direction. It is also possible to arrange straight cutting edges inclined with respect to the axial direction or to have one of the cutting edges running in an undulating configuration in the axial direction relative to a cylindrical surface. Since the cutting edges of the rotor may be knife edges, this allows the rotor, even before the shearing action is started, to dislodge from the vessel wall any deposits which are protruding or bulging into the shearing slot. The rotor is at least partially tapered in the direction of its front end and has at its front means to break up loose and solid deposits such as blood clots. This means may include a front face and two adjoining beveled surfaces lying opposite each other while the front face has on a circumference horn-like forwardly extending projections. This ensures that the rotor forces its way through the blood vessel in particular at stenosed or blocked sites. The stator and rotor may be made of metal although other materials such as suitable plastics may be used.

A guide wire which is preferably independent of the catheter extends therethrough. This facilitates the introduction of the catheter into the artery or vein by way of the guide wire which has already been introduced. The stator is connected to the tubular sheath serving as a catheter tube. It is also possible to fasten the stator in a movable manner at the tip or leading edge of the tubular sheath.

A further known catheter, the one from E-PB1-0,267,539, has as its cutting tool a substantially elliptical milling cutter which is provided with abrasive material on its surface and is driven at a speed of up to 160,000 rpm. The milling cutter is connected via a flexible drive shaft to a rotary drive mechanism which is arranged at the other end of the catheter. The drive shaft runs through a tubular sheath which serves as a catheter tube. A guide wire extending right through the drive shaft is introduced into the artery or vein before introduction of the catheter and is pushed forwards.

In this known rotary catheter, it is not possible to exclude the risk of the vessel wall being damaged, particularly at a curve, and in some cases even being drilled through.

Another known rotary catheter has a cutting tool which has two stripping blades and which is driven at a speed of 750 rpm. In this catheter, there is a risk that the stripping blades may, particularly at the relatively slow circumferential speed, pinch or tear or get caught in the vessel wall.

SUMMARY OF THE INVENTION

The invention is therefore based on the object of providing a catheter which is of the type mentioned at the outset and which on the one hand ensures that abnormal deposits in the blood vessels of humans are dislodged cleanly, and on the other hand makes damage to the vessel wall highly improbable.

The catheter according to the invention ensures that only deposits which are protruding and which come between the cutting edges can be caught and dislodged. The possibility of the vessel wall being damaged by the cutting tool is virtually ruled out here. Moreover, the risk of the cutting tool of such a catheter tearing and pinching the vessel wall is in practice eliminated by the shearing action in conjunction with the opposite cutting edge.

In a preferred embodiment the rotor attacks the deposits radially. This ensures that it is not possible, for example in the area of curves, to drill straight into the vessel wall.

Additional safety against damage to the vessel wall is afforded by another embodiment. By means of the provision of shearing slots, in the final analysis only those deposits which protrude into the shearing slots are detached.

Another embodiment guarantees a symmetry of the shearing action, since diametrically opposite sites on the vessel wall are attacked simultaneously. This results in a better concentric running of the rotor than would be possible if the latter were to attack the vessel wall only at one circumferential site.

Other Preferred Embodiments ensure that the cutting tools dislodge material about the whole circumference of the vessel wall, the stator being moved in such a way that the shearing slots arranged in it execute either a slowly revolving or reversible swivel movement about the longitudinal axis of the stator. With such a movement, the stator executes either a continuously helical movement, or a helical movement directed alternately to the left and to the right, during the advance. In the most straightforward case, such a movement can be effected manually by the attending physician if the stator, is connected to the tubular sheath in a manner fixed in terms of rotation and tensioning. In another preferred embodiment a uniformly revolving or reversible movement of the stator is guaranteed. The swivel drive mechanism necessary for this can be connected to the protruding rear end of the tubular sheath or, in a miniaturized configuration, can act directly on the stator. It is also possible to arrange a miniaturized reduction gear unit between the rotor and the stator in order to drive the stator by means of the rotational movement of the rotor, preferably in the opposite rotational direction in relation to the rotor.

Another preferred embodiment describes a particularly simple way of fastening the stator on the tubular sheath so that they are fixed in terms of rotation and tensioning.

Another preferred embodiment describes driving the rotor. It is also possible, however, to drive the rotor directly by means of a miniaturized gearing.

Another preferred embodiment permits immediate withdrawal of the deposits which have been detached and broken up, so as to avoid these deposits remaining in the bloodstream.

The efficacy of the conveyor screw is improved by another embodiment.

BRIEF DESCRIPTION OF THE DRAWINGS

An illustrative embodiment of the invention is explained in greater detail with reference to the drawings, in which:

FIG. 9 shows the head part of the catheter according to FIG. 1 in a perspective representation, viewed from the front end, and FIG. 10 shows the head part of the catheter according to FIG. 1 in a perspective representation, as seen from the drive side.

DISCUSSION OF THE PREFERRED EMBODIMENT

Figure 1:
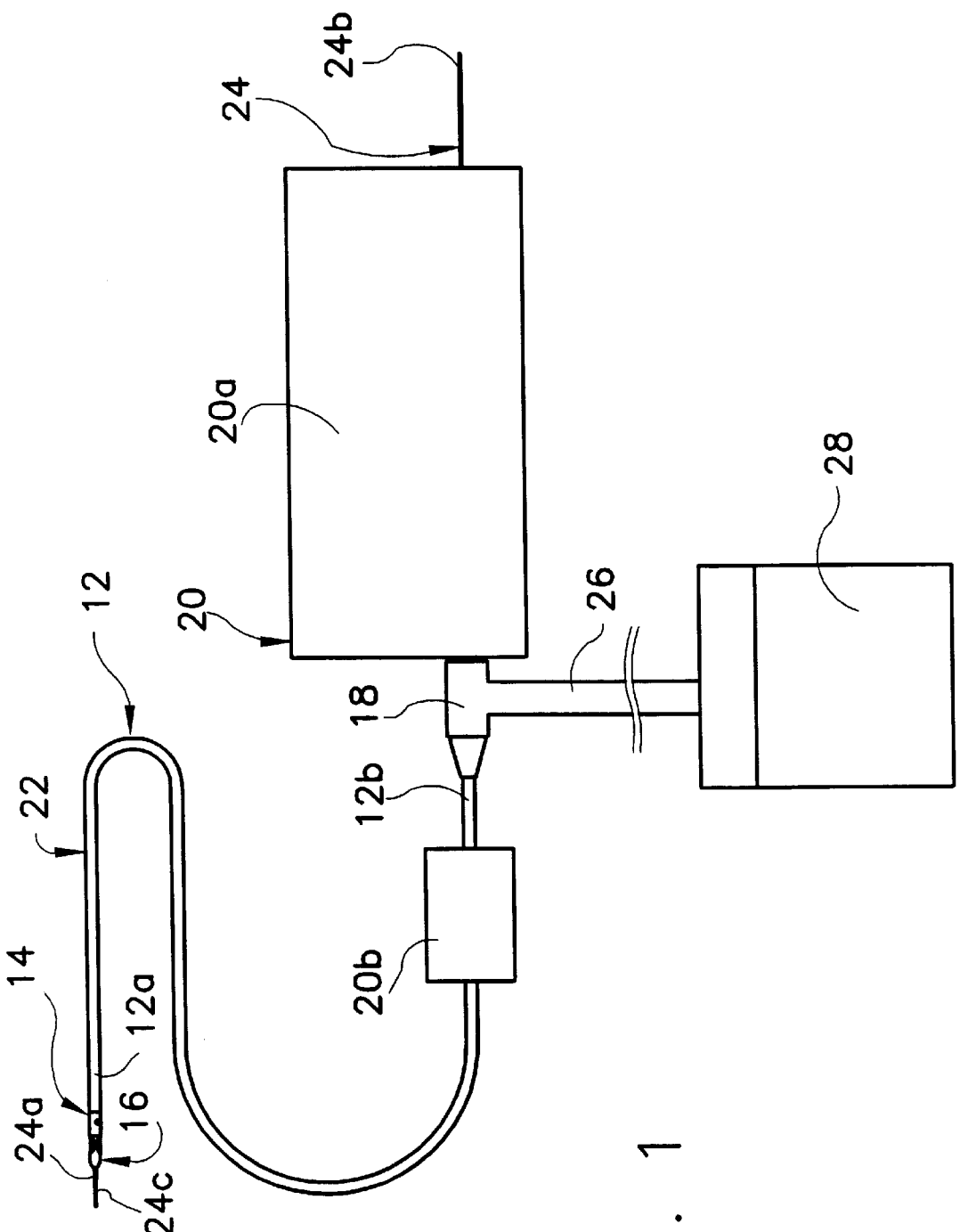
FIG. 1 shows a rotary catheter in a general view, with drive mechanism, guide wire and collection container for the deposit fragments which have been detached.

The catheter 12 shown in FIG. 1 has, at its front end 12a, a cutting tool which consists of a stator 14 and rotor 16. At its rear end 12b, the catheter 12 is connected to a rotary drive mechanism 20a of a drive unit 20 via a discharge chamber 18. A flexible drive shaft is mounted in a tubular sheath 22 serving as catheter tube and connects the rotor 16 to the rotary drive mechanism 20a. A guide wire 24 runs through the entire length of the catheter 12, and its front end 24a protrudes from the rotor 16 and its rear end 24b from the drive unit 20. A collection container 28 is linked to the discharge chamber 18 in the radial direction via a tube or a pipe 26.

The tubular sheath 22 is connected to a swivel drive mechanism 20b in a manner fixed in terms of rotation. This mechanism can be provided either for a revolving swivel movement or for a reversible swivel movement. Its speed lies substantially below that of the rotary drive mechanism 20a.

The swivel drive mechanism 20b can also be omitted if only the tubular sheath 22 is mounted in a rotatable manner. In such a configuration, the tubular sheath can be set by hand into a revolving or reversible swivel movement when the catheter 12, on being advanced, has reached the site which is to be treated.

It is also possible to uncouple the stator 14 from the tubular sheath 22 and for the stator 14 alone to be mounted so as to swivel, and to equip the stator directly with a miniaturized swivel drive mechanism (not shown).

When using the catheter 12, the guide wire 24 is introduced, with its front end 24a leading, into the artery or vein which is to be treated, and it is advanced as far as the stenosed area and then maneuvered through the latter, with radiographic monitoring. The catheter 12 is then passed along the guide wire 24. As soon as the rotor 16 has reached the area which is to be treated, the rotary drive mechanism 20a at least is switched on in order to detach the undesired deposits by means of the cutting tool. The speed of rotation of the rotor 16 preferably lies in the range of between 30,000 and 40,000 rpm. The catheter 12 is advanced slowly as the operation proceeds and in so doing is set in a slow swivel movement either by means of the swivel drive mechanism 20b or by hand. The deposits which have been dislodged and broken up are carried off through the tubular sheath 22 as far as the discharge chamber 18 and they pass from there into the collection container 28.

Figure 2:
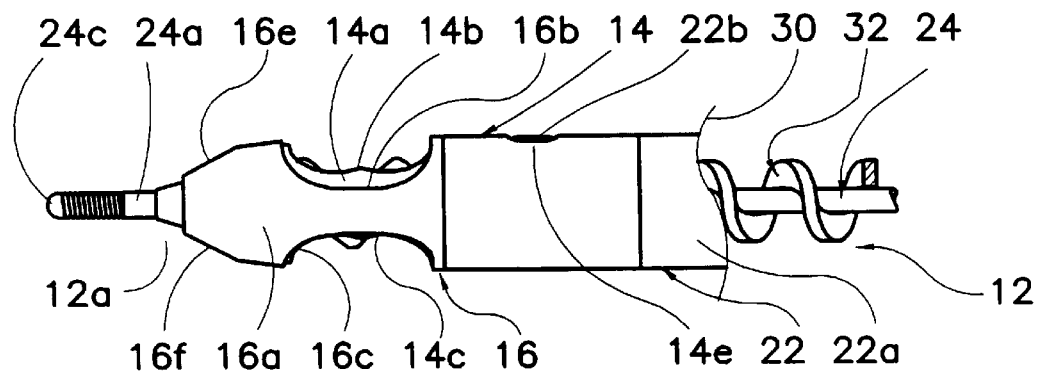
FIG. 2 shows an elevation of the head part of the rotary catheter according to FIG. 1, but on a larger scale.

FIG. 2 shows the front end 12a of the catheter 12 with its stator 14, its rotor 16 designed as external rotor, its tubular sheath 22, and the front end 24a of the guide wire 24. The tubular sheath 22 is shown cut away at 30 to reveal the flexible drive shaft 32 which, inside the rotor 16, is fixed to the latter in terms of rotation. The guide wire 24 extends through the inside of the drive shaft 32. The drive shaft 32 is additionally designed as a conveyor worm or conveyor screw in order to convey the deposits, which have been dislodged by the cutting tool 14, 16, through the tubular sheath 22 to the discharge chamber 18.

A portion 14a of the stator 14 extends into the rotor 16. It will be seen that the stator portion 14a and the rotor 16 engage one within the other like a bushing. The stator portion 14a has two shearing slots 14b, 14c which are offset 180° to each other about the circumference. The rotor 16 likewise has two slots 16b, 16c which are offset 180° to each other about the circumference.

Figure 3:
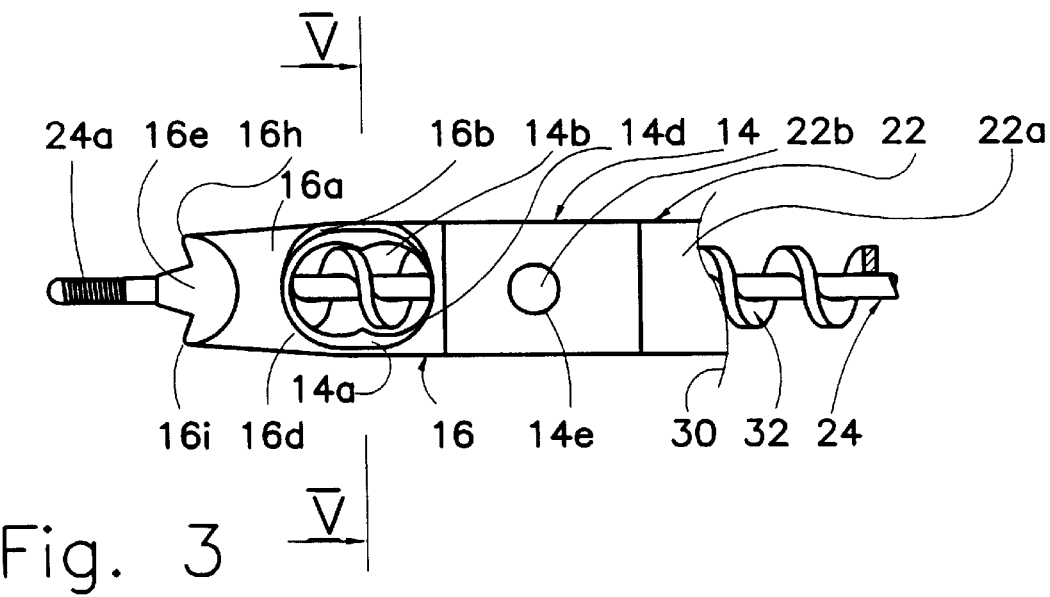
FIG. 3 shows the head part as in FIG. 2, but in a plan view.

From FIG. 3 it will be seen that the shearing slot 14b of the stator portion 14a is narrower than that 16b of the rotor 16 in the circumferential direction. One margin of the rotor slot 16b is designed as cutting edge 16d. The margin of the stator slot 14b, facing in the opposite direction, is designed as cutting edge 14d. This cutting edge 14d extends in an at least approximately undulating configuration.

The cutting edge 16d and the cutting edge 14d interact in a shearing action. Cutting edges of this type are in each case arranged in both slots 14b, 14c; 16b, 16c which are also referred to as shearing slots, in other words arranged 180° in relation to one another in the circumferential direction. The front end 16a of the rotor 16 tapers at least approximately conically. In this way, the stenosed area of the artery or vein to be treated is widened upon insertion of the catheter 12.

Figure 4:
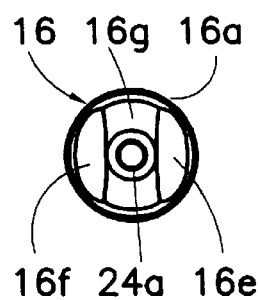
FIG. 4 shows an end view of the rotor and the guide wire of the rotary catheter according to FIG. 3.

FIG. 4 shows the front elevation of the rotor 16 and of the front end 24a of the guide wire 24. Also shown are two beveled surfaces 16e, 16f of the rotor 16, which surfaces run in opposite directions and between which there is a front face 16g. The front face 16g has, on the circumference, horn-like, forwardly extending projections 16h, 16i (FIG. 3). The front of the rotor 16 serves in particular to break up clots obstructing the passage, in order to force a path for the catheter 12 along the blood vessel.

Figure 5:
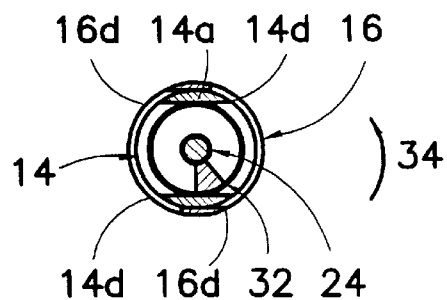
FIG. 5 shows the head part in cross-section along the cutting line V—V in FIG. 3.

FIG. 5 shows a cross-section along V—V in FIG. 3. The rotor 16 is driven in the direction of the arrow 34. The cutting edges 16d of the rotor 16 in this case attack via the circumference the deposits, for example the stenoses, and break these up. The cutting edges 14d of the stator portion 14a achieve a shearing action in conjunction with the cutting edges 16d of the rotor, with the sheared-off fragments of the deposits passing into the region of the drive shaft 32 and conveyor screw and being conveyed onwards from there as far as the discharge chamber 18 (FIG. 1). In this representation it should be noted that the external diameter of the rotor 16 is less than 3 mm.

The rotor 16 and the stator 14 are preferably made of metal. The guide wire 24 is a steel wire with nib tip 24c. The drive shaft 32 also serving as conveyor worm or conveyor screw consists of a coated steel wire, for example. The tubular sheath 22 is preferably made of plastic.

For connecting the stator 14 to the tubular sheath 22 in a rotationally fixed manner, the front end 22a of the latter (FIGS. 2 and 3) is press-fitted into the stator 14, for example. For securing purposes, holes 14e are arranged in the circumferential surface of the stator 14, and the pressed-in tube material 22b swells slightly into said holes 14e.

Figure 6:
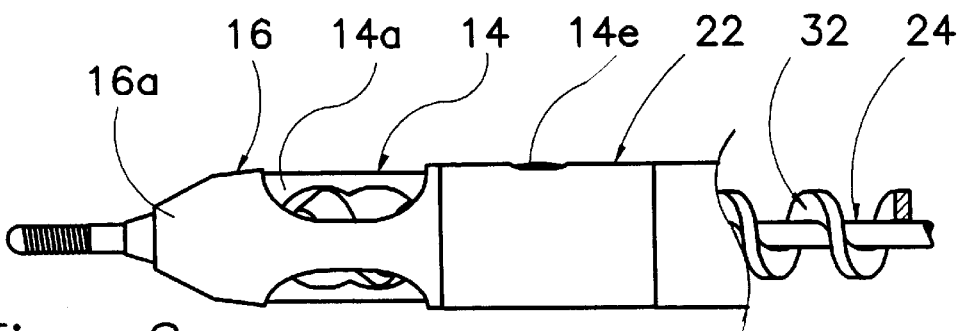
FIG. 6 shows the rotary catheter according to FIG. 3, but with the rotor turned through 90° relative to the stator.

In the view according to FIG. 6, the position of the stator 14 corresponds to that in FIG. 3, and the position of the rotor 16 corresponds to that in FIG. 2. The slight difference in diameter between the stator portion 14a and the rotor 16 is clearly visible here.

Figure 7:
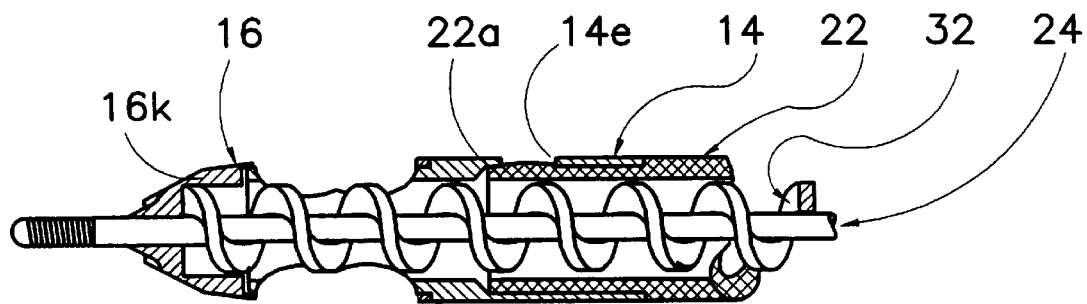
FIG. 7 shows a longitudinal section through the head part of the rotary catheter according to FIG. 2.

From the longitudinal section according to FIG. 7, it can be seen in particular that the drive shaft 32 extends with its front end 32a into the head part 16k of the rotor 16 and is there connected to the latter in a manner fixed in terms of rotation, for example press-fitted into it. It can also be seen how the tubular sheath 22 is secured in the stator 14 via the holes 14e, in a manner fixed in terms of rotation and tensioning.

Figure 8:
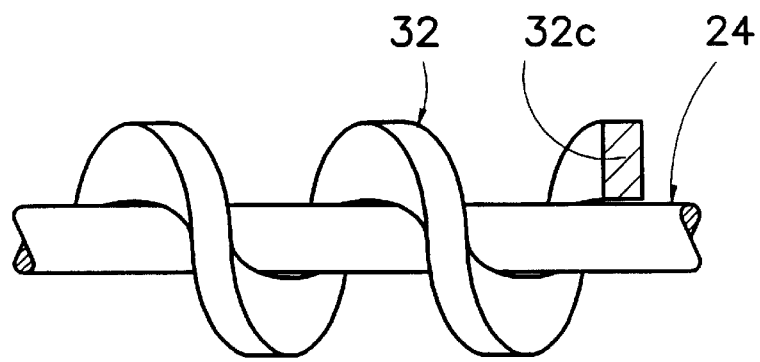
FIG. 8 shows guide wire and helical winding, in a cross-section through the helical winding.

FIG. 8 shows in particular the rectangular cross-section of the wire 32c of the helical drive shaft 32 which at the same time also serves as conveyor worm or conveyor screw. The arrangement of the guide wire 24 coaxially inside the drive shaft 32 results in a particularly high degree of efficacy as conveyor worm or conveyor screw. The dislodged fragments of the deposits are conveyed in a virtually linear manner inside the tubular sheath 22.

FIGS. 9 and 10 show all the parts already described, but in a perspective representation.

We claim:

1. A catheter for detaching abnormal deposits from blood vessels in humans comprising:
   a cutting tool comprising a stator and a rotor, said rotor surrounding a portion of said stator, said rotor and said stator configured to allow relative rotational motion between said rotor and said stator, said rotor including a rotor cutting edge arranged in a circumferential surface of said rotor, said stator including a stator cutting edge arranged in a circumferential surface of said stator, wherein said stator cutting edge is configured to oppose said rotor cutting edge so as to produce a shearing action between said stator cutting edge and said rotor cutting edge when said rotor is rotated relative to said stator;
   a rotary drive mechanism configured to rotate said rotor; and
   a tubular sheath communicating with said cutting tool, said sheath defining a discharge path for deposits detached by said cutting tool.

2. A catheter according to claim 1, wherein said rotor is substantially cylindrical in a portion including said rotor cutting edge and said stator is substantially cylindrical in a portion including said stator cutting edge.

3. A catheter according to claim 1, wherein said rotor further comprises a first rotor shearing slot provided in said circumferential surface of said rotor and which includes said rotor cutting edge, and wherein said stator further comprises a first stator shearing slot provided in said circumferential surface of said stator which includes said stator cutting edge.

4. A catheter according to claim 3, wherein said rotor further comprises a second rotor shearing slot provided in said circumferential surface of said rotor 180° from said first rotor shearing slot, and wherein said stator further comprises a second stator shearing slot provided in said circumferential surface of said stator 180° from said first stator shearing slot.

5. A catheter according to claim 1, wherein said rotor cutting edge and said stator cutting edge extend at least substantially in an axial direction of said cutting tool.

6. A catheter according to claim 1, wherein at least one of said rotor cutting edge and said stator cutting edge includes at least one undulation along an axial direction of said cutting tool.

7. A catheter according to claim 1, wherein said rotor cutting edge and said stator cutting edge are knife edges.

8. A catheter according to claim 1, wherein said rotor is at least partially tapered in a direction of a front end of said rotor.

9. A catheter according to claim 8, wherein said rotor includes means for breaking up loose and solid deposits, said means for breaking provided on the front end of said rotor.

10. A catheter according to claim 9, wherein said means for breaking up loose and solid deposits comprises a front face, a first and a second beveled surface adjacent said front face, wherein said front face includes forwardly extending projections.

11. A catheter according to claim 1, wherein at least one of said stator and said rotor is constructed of a metal.

12. A catheter according to claim 1, further comprising a flexible drive shaft connecting said rotary drive mechanism with said rotor, and a guide wire, wherein said guide wire is provided within said flexible drive shaft and wherein said guide wire extends through said tubular sheath.

13. A catheter according to claim 1, wherein said stator is fixed to said tubular sheath, wherein said tubular sheath serves as a catheter tube.

14. A catheter according to claim 13, wherein said stator includes at least one hole for anchoring said tubular sheath, said sheath being press-fitted into said stator and wherein said sheath is made of plastic.

15. A catheter according to claim 1, wherein said stator is configured to rotate around its longitudinal axis.

16. A catheter according to claim 15, wherein said stator is configured to rotate over a range of rotation such that said cutting tool can remove deposits over 360° of a circumference of said cutting tool.

17. A catheter according to claim 15, wherein said stator or said tubular sheath is connected to a swivel drive mechanism, wherein an output speed of said swivel drive mechanism is substantially below that of said rotary drive mechanism.

18. A catheter according to claim 1, wherein said rotary drive mechanism is connected to said rotor by a flexible drive shaft, wherein said flexible drive shaft is provided within said tubular sheath.

19. A catheter according to claim 18, wherein said flexible drive shaft has a helical shape such that when said shaft is rotated relative to said tubular sheath, said shaft conveys broken-up deposits towards said rotary drive mechanism.

20. A catheter according to claim 19, wherein a guide wire extends through said flexible drive shaft.

* * * * *